(12) United States Patent
Li et al.

(10) Patent No.: US 7,799,813 B2
(45) Date of Patent: Sep. 21, 2010

(54) SALTS OF SUBSTITUTED 5-MEMBERED AZACYCLE AND USE THEREOF IN THE TREATMENT OF DISEASES RELATED TO PROTEIN AGING

(75) Inventors: Song Li, Beijing (CN); Hao Cui, Beijing (CN); Junhai Xiao, Beijing (CN); Wu Zhong, Beijing (CN); Lili Wang, Beijing (CN); Gang Cheng, Beijing (CN)

(73) Assignee: Beijing Molecule Science and Technology Co., Ltd., Beijing (CN)

( * ) Notice: Subject to any disclaimer, the term of this patent is extended or adjusted under 35 U.S.C. 154(b) by 0 days.

(21) Appl. No.: 12/223,236

(22) PCT Filed: Jan. 29, 2007

(86) PCT No.: PCT/CN2007/000319

§ 371 (c)(1),
(2), (4) Date: Nov. 18, 2008

(87) PCT Pub. No.: WO2007/085203

PCT Pub. Date: Aug. 2, 2007

(65) Prior Publication Data

US 2009/0227643 A1     Sep. 10, 2009

(30) Foreign Application Priority Data

Jan. 27, 2006    (CN) .................. 2006 1 0002391

(51) Int. Cl.
C07D 277/60    (2006.01)
C07D 277/30    (2006.01)
A61K 31/428    (2006.01)
A61K 31/426    (2006.01)

(52) U.S. Cl. .................. 514/365; 548/180; 548/204; 514/367

(58) Field of Classification Search .......... 548/204, 548/180
See application file for complete search history.

(56) References Cited

U.S. PATENT DOCUMENTS

| 5,580,904 | A | 12/1996 | Ishikura et al. |
| 5,656,261 | A * | 8/1997 | Cerami et al. .................. 424/53 |
| 5,853,703 | A | 12/1998 | Cerami et al. |
| 6,007,865 | A | 12/1999 | Cerami et al. |
| 6,440,749 | B1 | 8/2002 | Cerami et al. |
| 6,458,819 | B1 | 10/2002 | Wagle et al. |
| RE38,330 | E | 11/2003 | Cerami et al. |
| 6,960,605 | B2 | 11/2005 | Wagle et al. |
| 7,022,719 | B2 | 4/2006 | Cerami et al. |
| 2002/0022622 | A1 | 2/2002 | Wagle et al. |
| 2002/0055527 | A1 | 5/2002 | Wagle et al. |
| 2002/0068729 | A1 | 6/2002 | Egan et al. |
| 2002/0192842 | A1 | 12/2002 | Cerami et al. |
| 2004/0034074 | A1 | 2/2004 | Cerami et al. |
| 2005/0137215 | A1* | 6/2005 | Guzzo et al. ............. 514/265.1 |
| 2006/0014781 | A1 | 1/2006 | Wagle et al. |

FOREIGN PATENT DOCUMENTS

| CN | 1185736 A | 6/1998 |
| CN | 1406127 A | 3/2003 |
| CN | 1426303 A | 6/2003 |
| CN | 1534027 A | 10/2004 |
| CN | 1534028 A | 10/2004 |

OTHER PUBLICATIONS

Washabaugh et al. Biochemistry 1988, 27, 5044-53.*
Dupont et al. Acta Cryst. 1989, 45, 1926-1928.*
CAPLUS record of U.S. Patent No. 5,656,261, Published 1996.*
Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*

(Continued)

*Primary Examiner* — Rebecca L Anderson
*Assistant Examiner* — Matthew P Coughlin
(74) *Attorney, Agent, or Firm* — Harness, Dickey & Pierce, P.L.C.

(57) ABSTRACT

The present invention relates to 5-membered azacycle compounds of formula (I), pharmaceutically acceptable salts thereof and hydrates thereof, wherein the groups are as defined in the specification. The present invention further relates to pharmaceutical compositions containing said compounds or pharmaceutically acceptable salts thereof or hydrates thereof, and to use of the pharmaceutical compositions in (i) improving skin elasticity or reducing skin wrinkles, (ii) treating diabetes, (iii) treating or relieving adverse sequelae of diabetes, (iv) treating or relieving kidney damage, (v) treating or relieving damage to blood vasculature, (vi) treating or relieving hypertension, (vii) treating or relieving retinopathy, (viii) treating or relieving damage to lens proteins, (ix) treating or relieving cataract, (x) treating or relieving peripheral neuropathy, or (xi) treating or relieving osteoarthritis. The present invention further relates to use of said compounds or pharmaceutically acceptable salts thereof or hydrates thereof in the preparation of oral formulations for inhibiting or reversing tooth staining, or in the preparation of fresh-keeping agents for plant proteins of crops or animal proteins.

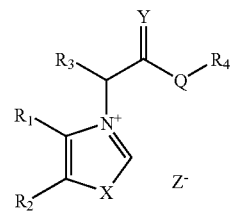

(I)

5 Claims, No Drawings

OTHER PUBLICATIONS

European Search Report dated Jun. 2, 2009 in corresponding EP Application No. 07710857.9.
Yurkevich, et al., "Thiazole derivatives with a 3-N-methylene bridge", Chemistry of Heterocyclic Compounds, vol. 4, No. 4, 1968, pp. 559-559, XP002507283, New York, NY, US.
Potts, et al., "Bridgehead nitrogen systems. X. Cycloadditions with thiazolium N-ylides", The Journal of Organic Chemistry, vol. 41, No. 2, 1976, pp. 187-191, XP008099453.
Ikeda Hiroshi, et al., "Artificial holoenzymes for benzoin condensation using thiazolio-appended beta-cyclodextrin dimers", Tetrahedron Letters, vol. 41, No. 33, Aug. 12, 2000, pp. 6483-6487, XP002507284, ISSN: 0040-4039.
Cheng G, et al., "Beneficial effects of C36, a novel breaker of advanced glycation endproducts cross-links, on the cardiovascular system of diabetic rats", vol. 152, No. 8, Dec. 2007, pp. 1196-1206, XP002507285, ISSN: 0007-1188.

Examination and Search Report dated Feb. 6, 2009 in the corresponding EP Application No. 07 710 857.9-1211.
Examination Report dated Jan. 19, 2010 in the corresponding EP Application No. 07 710 857.9-1211.
Yurkevich et al: "Thiazole Derivatives with a 3-N-methylene bridge" Chemistry of Heterocyclic Compounds, vol. 4, No. 4, 1968, pp. 559-559, XP002507283 New York, NY, United States.
Potts et al: "Bridgehead nitrogen systems." The Journal of Organic Chemistry, vol. 41, No. 2, 1976, pp. 187-191, XP008099453.
Ikeda Hiroshi et al: "Artificial holoenzymes for benzoin condensation using thiazolio-appended beta-cyclodextrin dimers" Tetrahedron Letters, vol. 41, No. 33, Aug. 12, 2000, pp. 6483-6487, XP002507284 ISSN: 0040-4039.
Cheng G et al: "Beneficial effects of C36, a novel breaker of advanced glycation endproducts cross-links, on the cardiovascular system of diabetic rats" British Journal of Pharmacology, vol. 152, No. 8, Dec. 2007, pp. 1196-1206, XP002507285 ISSN: 0007-1188.

* cited by examiner

SALTS OF SUBSTITUTED 5-MEMBERED AZACYCLE AND USE THEREOF IN THE TREATMENT OF DISEASES RELATED TO PROTEIN AGING

CROSS-REFERENCE TO RELATED APPLICATIONS

This application is a U. S. National Stage Application of International application No. PCT/CN2007/000319, filed 29 Jan. 2007, and published in Chinese as WO 2007/085203 A1 on 2 Jul. 2007. This application claims the benefit of Chinese Patent Application No. 200610002391.6, filed 27 Jan. 2006) The disclosures of the above applications are incorporated herein by reference.

TECHNICAL FIELD

The present invention relates to salt compounds of substituted 5-membered azacycle, the preparation thereof, pharmaceutical compositions containing the same, and the use thereof in the prevention or treatment of diseases or symptoms related to AGEs, including (i) improving skin elasticity or reducing skin wrinkles, (ii) treating diabetes, (iii) treating or relieving adverse sequelae of diabetes, (iv) treating or relieving kidney damage, (v) treating or relieving damage to blood vasculature, (vi) treating or relieving hypertension, (vii) treating or relieving retinopathy, (viii) treating or relieving damage to lens proteins, (ix) treating or relieving cataract, (x) treating or relieving peripheral neuropathy, and (xi) treating or relieving osteoarthritis.

BACKGROUND ART

The reaction between sugars and proteins has been known for some time. As early as the year 1912, Maillard found that glucose and other reducing sugars reacted with amino acids, then stable brown pigments were formed through a series of dehydrations and rearrangements. Further studies have suggested that storing and heat-treating food could also produce such pigments formed from sugars and polypeptides. The formation of such pigments reduces the biological activity of proteins. For related application patents, please see U.S. Ser. No. 08/588,249. The non-enzymatic reaction between reducing sugars and free amino acids can form a stable diketone byproduct, known as the Amadori product. In particular, the amino terminal of the beta-chain of hemoglobin reacts with glucose to form hemoglobin A1c. Like reactions have been found to occur with a variety of other body proteins, such as lens crystallins, collagen and nerve proteins. See, Advanced Glycosylation; Chemistry, Biology and Implications for Diabetes and Aging, Advances in Pharmacology, Vol. 23, pp. 1-34 Academic Press, 1992).

Said reactions are accelerated in the presence of elevated glucose levels, as occur in individuals with diabetes mellitus, but still occur at normal glucose levels. Meanwhile, the aging process is closely related to the formation of lipofuscin. The aging of collagen can be mimicked in vitro by using collagen and glucose. The glucose-induced collagen products capture and react with other proteins, leading to a cross-linking reaction between the proteins. The glucose induced crosslinking reaction produces advanced glycosylation endproducts (AGEs). It is known that AGEs are related to the complications of diabetes, and normal aging process also gives rise to the increase of AGEs. The AGEs inside the body not only have aberrant pathological chemical structure but also can be identified by certain receptors, and thus cause complicated pathological changes related to diabetes and aging.

At present, several successful therapeutic approaches have been achieved based upon intervening in the accumulation of AGEs. One approach is described in U.S. Pat. No. 4,758,583, wherein aminoguanidine and the analogues thereof are used to inhibit the formation of AGEs from its precursors. By reacting with early glycosylation products, the agents prevent the glycosylation products from being further converted into AGEs, and further cross-linking of AGEs with tissues is also inhibited. Efficacy of this approach has been demonstrated in rat animal models of diabetes and aging, including other effects on macrovascular, renal and neural pathology. These data have been reviewed by Vlassara, et al., 1994, Biology of Diseases, "Pathogenic effects of advanced glycosylation: biochemical, biologic and clinical implications for diabetes and aging", Laboratory Investigation 70:138-151; Brownlee, 1995, "The pathological implications of protein glycation", Clin. Invest. Med., 18:275-281; and Brownlee, 1995, "Advanced protein glycosylation in diabetes and aging", Ann. Rev. Med. 46:223-34.

Another approach for controlling AGEs in tissues, especially AGE cross-links (which are responsible for clinical or subclinical pathological changes) that have already been formed and accumulated in tissues, is to reverse or break the formed AGE cross-links. Vassan et al. have proved that this approach involving the breaking of AGEs is effective (vassan, et al., Nature, 1996, Vol. 382(18), 275-278). All of the compounds, formulations and methods disclosed in U.S. Pat. No. 5,656,261 and U.S. application Ser. Nos. 08/588,249 and U.S. Ser. No. 08/848,776 can break the formed AGE cross-links in vivo and in vitro. Studies have demonstrated positive effects of such compounds on cardiovascular diseases resulted from aging (Wolffenbuttel, et al., 1998, "Breakers of Advanced Glycation End Products Restores Large Artery Properties in Experimental Diabetes", Proc. Nat. Acad. Sci. U.S.A. 95:4630-4634). In these studies, rats diabetic for 9 weeks followed by 1 to 3 weeks administration of an AGE breaker compound resulted in reversal of diabetes-induced increases in large artery stiffness. Parameters that were improved included cardiac output, peripheral resistance, systemic arterial compliance, input impedance of the aorta, and compliance of the carotid artery (U.S. Pat. No. 6,319,934).

DISCLOSURES OF THE INVENTION

The object of the invention is to search for and develop a small molecular breaking agent, which acts on AGEs to break the already-formed AGEs so as to prevent protein cross-linking and break the cross-linked proteins, to thereby promote protein metabolism and treat or prevent various pathological changes resulted from the elevated level of AGEs in vivo. The present invention may be used for increasing skin elasticity or reducing skin wrinkles, treating diabetes, or treating or relieving adverse sequelae of diabetes, kidney damage, damage to blood vasculature, hypertension, retinopathy, damage to lens proteins, cataract, peripheral neuropathy, or osteoarthritis. The glycosylated proteins, on which the breaking agent of cross-linked protein acts, are not limited to human proteins, but also include plant proteins of crops or animal proteins, thus the breaking agent can be further used for the fresh-keeping of plant proteins of crops and animal proteins.

The inventors have found that compounds of the following general formula (I) can be used for the treatment and/or prevention of various diseases resulted from protein glycosylation.

The inventors have found that, compared with the preferred compound ALT-711 disclosed in U.S. Pat. No. 5,656,261, the compounds of the general formula (I) have better AGE breaking activity and lower toxicity, as shown on various models in vivo and in vitro.

Thus, in one aspect, the present invention relates to a compound of general formula (I),

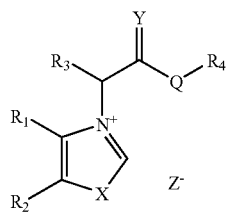

wherein:

X is O or S,

Y is O or S,

Q is O or NH, $R_1$ and $R_2$ can be the same or different, and are independently selected from the group consisting of hydrogen, $C_1$-$C_4$ alkyl, $C_2$-$C_4$ alkenyl, and hydroxy-$C_1$-$C_4$ alkyl, or $R_1$ and $R_2$ are bonded to form an aromatic ring $Ar_2$ or a 5- or 6-membered aliphatic ring, $R_3$ is hydrogen, a linear or branched $C_1$-$C_8$ alkyl, a linear or branched $C_2$-$C_8$ alkenyl, a $C_3$-$C_8$ cycloalkyl, hydroxy, a $C_1$-$C_4$ alkoxy, a $C_1$-$C_4$ alkylamino, cyano, or trifluoromethyl, $R_4$ is hydrogen, a linear or branched $C_1$-$C_8$ alkyl, a linear or branched $C_2$-$C_8$ alkenyl, a $C_3$-$C_8$ cycloalkyl, or a mono-, di-, or tricyclic aromatic homocycle or heterocycle radical, wherein each ring consists of 5 to 6 ring atoms, the heterocycle radical contains 1 to 6 heteroatoms selected from the group consisting of O, S and N, the rings are independently unsubstituted or substituted with 1 to 3 substituents selected from the group consisting of halogen, nitro, hydroxy, hydroxymethyl, trifluoromethyl, trifluoromethoxy, linear or branched $C_1$-$C_6$ alkyl, linear or branched $C_2$-$C_6$ alkenyl, $C_1$-$C_4$ alkoxy, $C_2$-$C_4$ alkenoxy, phenoxy, benzyloxy, carboxy, and amino, and $Z^-$ is a pharmaceutically acceptable acid radical, or a pharmaceutically acceptable salt thereof or a hydrate thereof.

In a preferred embodiment, the present invention relates to a compound of general formula (I),

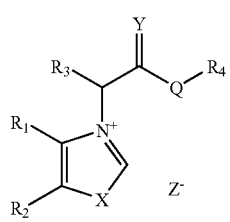

wherein:

X is S,

Y is O or S,

Q is O or NH, $R_1$ and $R_2$ can be the same or different, and are independently selected from the group consisting of hydrogen, $C_1$-$C_4$ alkyl, and $C_2$-$C_4$ alkenyl; or $R_1$ and $R_2$ are bonded to form an aromatic ring $Ar_2$, $R_3$ is hydrogen, a linear or branched $C_1$-$C_8$ alkyl, a linear or branched $C_2$-$C_8$ alkenyl, a $C_3$-$C_8$ cycloalkyl, hydroxy, a $C_1$-$C_4$ alkoxy, a $C_1$-$C_4$ alkylamino, cyano, or trifluoromethyl, $R_4$ is hydrogen, a linear or branched $C_1$-$C_8$ alkyl, a linear or branched $C_2$-$C_8$ alkenyl, a $C_3$-$C_8$ cycloalkyl, or a mono-, di-, or tricyclic aromatic homocycle or heterocycle radical, wherein each ring consists of 5 to 6 ring atoms, the heterocycle radical contains 1 to 6 heteroatoms selected from the group consisting of O, S and N, the rings are independently unsubstituted or substituted with 1 to 3 substituents selected from the group consisting of halogen, nitro, hydroxy, hydroxymethyl, trifluoromethyl, trifluoromethoxy, linear or branched $C_1$-$C_6$ alkyl, linear or branched $C_2$-$C_6$ alkenyl, $C_1$-$C_4$ alkoxy, $C_2$-$C_4$ alkenoxy, phenoxy, benzyloxy, carboxy, and amino, and $Z^-$ is a pharmaceutically acceptable acid radical, or a pharmaceutically acceptable salt thereof or a hydrate thereof.

In a more preferred embodiment, the present invention relates to a compound of formula (I),

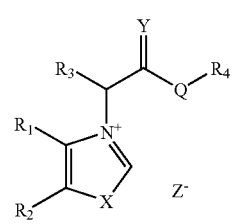

wherein:

X is S,

Y is O,

Q is O, $R_1$ is methyl, or is bonded with $R_2$ to form a 6-membered aliphatic ring, $R_2$ is methyl or hydroxyethyl, or is bonded with $R_1$ to form a 6-membered aliphatic ring, $R_3$ is hydrogen, $R_4$ is hydrogen or benzyl, and $Z^-$ is a pharmaceutically acceptable acid radical, such as $F^-$, $Cl^-$, $Br^-$, $I^-$, methanesulfonate, or p-methylbenzenesulfonate, and preferably $Br^-$ or methanesulfonate, or a pharmaceutically acceptable salt thereof or a hydrate thereof.

The compounds of the present invention include, but are not limited to:

| Compound | Name | Structure | m.p. ° C. |
|---|---|---|---|
| 1 | 3-benzyloxycarbonylmethyl-4,5-dimethyl-thiazole-3-bromide | 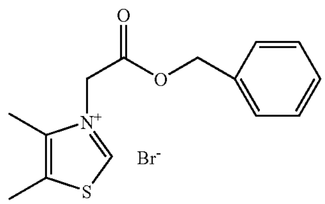 | oil |
| 2 | 3-benzyloxycarbonylmethyl-5-(2-hydroxyethyl)-4-methyl-thiazole-3-bromide | 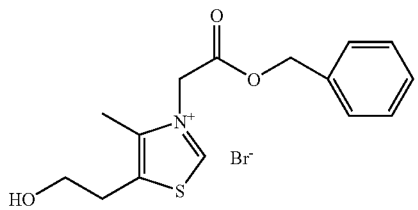 | oil |
| 3 | 3-benzyloxycarbonylmethyl-4-methyl-thiazole-3-bromide | 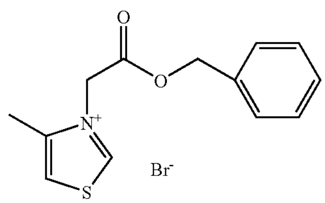 | 217-218 |
| 4 | 3-benzyloxycarbonylmethyl-4,5,6,7-tetrahydro-benzothiazole-3-bromide | 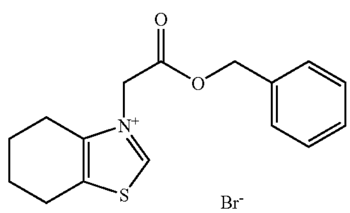 | 160-166 |
| 5 | 3-carboxymethyl-4-methyl-thiazole-3-bromide | | 223-230 | or pharmaceutically acceptable salts thereof or hydrates thereof.

Among the above compounds, 3-benzyloxycarbonylmethyl-4-methyl-thiazole-3-bromide is more preferred.

In accordance with the present invention, the pharmaceutically acceptable salts of the compounds of the present invention include inorganic acid salts or organic acid salts, including but not limited to: chloride, bromide, iodide, nitrate, sulfate, bisulfate, phosphate, hydrogen phosphate, acetate, propionate, butyrate, oxalate, trimethylacetate, adipate, alginate, lactate, citrate, tartrate, succinate, maleate, fumarate, picrate, aspartate, gluconate, benzoate, methanesulfonate, ethanesulfonate, benzenesulfonate, p-methyl benzenesulfonate, and dihydroxy naphthalene carboxylate.

In another aspect, the present invention relates to a method for preparing the compound of the formula (I) or pharmaceutically acceptable salts thereof or hydrates thereof, comprising the steps of a) reacting sulfourea or urea of the following formula

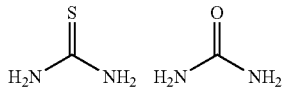

with a ketone of formula (II)

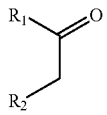
(II)

wherein $R_1$ and $R_2$ are as defined above for the compounds of the formula (I), in the presence of a halogen as a catalyst, to form a compound of formula (III), or following the method described in the literature, J. Amer. Chem. Soc., 1949, 71, 4007, to conduct a reaction in the presence of a halogen as a catalyst to obtain a compound of the formula (III),

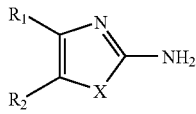
(III)

wherein $R_1$, $R_2$ and X are as defined above for the compound of the formula (I), b) reacting the compound of the formula (III) with isoamyl nitrite to form a compound of formula (IV),

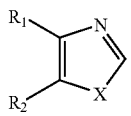
(IV)

wherein $R_1$, $R_2$ and X are as defined above, c) reacting the compound of the formula (IV) with a compound of formula (V),

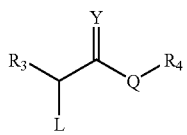
(V)

wherein $R_3$, Y, Q and $R_4$ are as defined above for the compound of the formula (I), and L is a leaving group, such as F, Cl, Br, I, methanesulfonato, or p-methylbenzenesulfonato, to form the compound of the formula (I)

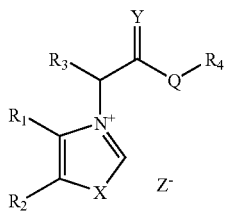
(I)

wherein $R_1$, $R_2$, $R_3$, X, Y, Q, $R_4$ and Z are as defined above, optionally, further hydrolyzing the compound of the formula (I), where $R_4$ is not H, to obtain a compound of formula (Ia):

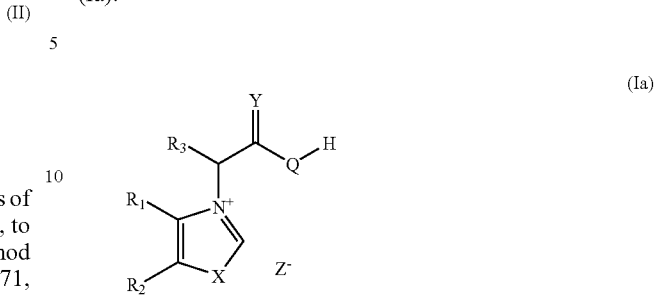
(Ia)

wherein $R_1$, $R_2$, $R_3$, X, Y, Q and Z are as defined above, optionally, reacting the compound of the formula (Ia), where Q is O, with a linear or branched $C_1$-$C_8$ alkanol, a linear or branched $C_2$-$C_8$ alkenyl alcohol, a $C_3$-$C_8$ cycloalkyl alcohol, or an aromatic alcohol, to obtain an ester.

When needed, the obtained compounds can be converted from one salt into another salt according to methods known per se.

In an embodiment, the compounds of the present invention can be prepared by the following reaction route:

Reaction route I:

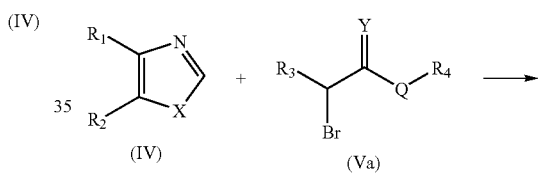

comprising reacting a compound of formula (IV)

(IV)

wherein,

X is O or S, $R_1$ and $R_2$ can be the same or different, and are independently selected from the group consisting of hydrogen, $C_1$-$C_4$ alkyl and $C_2$-$C_4$ alkenyl; or $R_1$ and $R_2$ are linked together to form an aromatic ring $Ar_2$, with a compound of formula (Va)

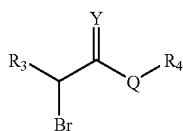
(Va)

wherein,

Y is O or S,

Q is O or NH, $R_3$ is hydrogen, a linear or branched $C_1$-$C_8$ alkyl, a linear or branched $C_2$-$C_8$ alkenyl, a $C_3$-$C_8$ cycloalkyl, hydroxy, a $C_1$-$C_4$ alkoxy, a $C_1$-$C_4$ alkylamino, cyano, or trifluoromethyl, $R_4$ is hydrogen, a linear or branched $C_1$-$C_8$ alkyl, a linear or branched $C_2$-$C_8$ alkenyl, a $C_3$-$C_8$ cycloalkyl, or a mono-, di-, or tricyclic aromatic homocycle or heterocycle radical, wherein each ring consists of 5 to 6 ring atoms, the heterocycle radical contains 1 to 6 heteroatoms selected from the group consisting of O, S and N, the rings are independently unsubstituted or substituted with 1 to 3 substituents selected from the group consisting of halogen, nitro, hydroxy, hydroxymethyl, trifluoromethyl, trifluoromethoxy, linear or branched $C_1$-$C_6$ alkyl, linear or branched $C_2$-$C_6$ alkenyl, $C_1$-$C_4$ alkoxy, $C_2$-$C_4$ alkenoxy, phenoxy, benzyloxy, carboxy, and amino, to form a compound of general formula (I)

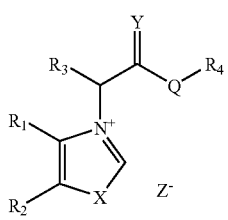
(I)

wherein X, Y, Q, $R_1$, $R_2$, $R_3$, and $R_4$ are as defined above, and $Z^-$ is $Br^-$.

In the above reaction route, the reaction between the compound of the formula (IV) and the compound of the formula (Va) is conducted in the presence of a solvent, such as ethanol, acetonitrile or butanone, or in the absence of a solvent when one of the above two raw materials is a liquid, at a temperature of 80° C. to 100° C. under nitrogen atmosphere for 5 to 96 hours.

The reaction product can be purified by using still standing crystallization and then recrystallization or by using silica gel column chromatography. The silica gel useful in the invention can be conventional silica gel for chromatography with a particle size of from 10 to 40 μm, and the eluent can be formulated from one or several solvents, and preferably is one of mixed solvents formulated from dichloromethane and methanol in different proportions. After purification, the compound of the formula (I) according to the present invention is obtained.

The compounds of the formula (IV) used according to the above reaction route are known, or can be synthesized by many methods, such as one according to reaction route II.

Reaction route II:

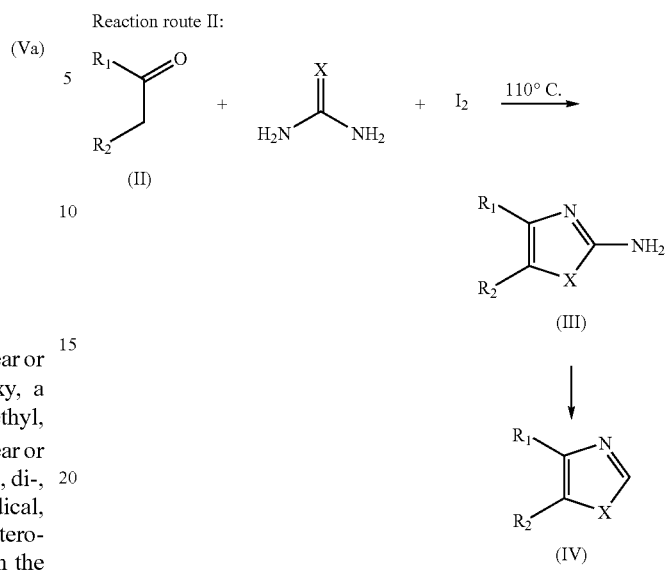

wherein $R_1$, $R_2$, and X are as defined above for the compound of the formula (I).

According to the above reaction route II, a compound of the formula (II) reacts with urea or sulfourea in the presence of iodine to form a compound of the formula (III), then the compound of the formula (III) is treated with isoamyl nitrite in anhydrous tetrafuran, to form a compound of the formula (IV) by removing the amino group. The compound of the formula (IV) can be purified by high vacuum distillation or silica gel chromatography, wherein the silica gel used can be conventional silica gel for chromatography with a particle size of from 10 to 40 μm, and the eluent can be formulated from one or several solvents, and preferably is one of mixed solvents formulated from ethyl acetate and cyclohexane in different proportions.

The compounds of the formula (Va) used according to the above reaction route I are known, or can be synthesized by methods known per se. For example, the compounds of the formula (Va) can be synthesized by the following methods:

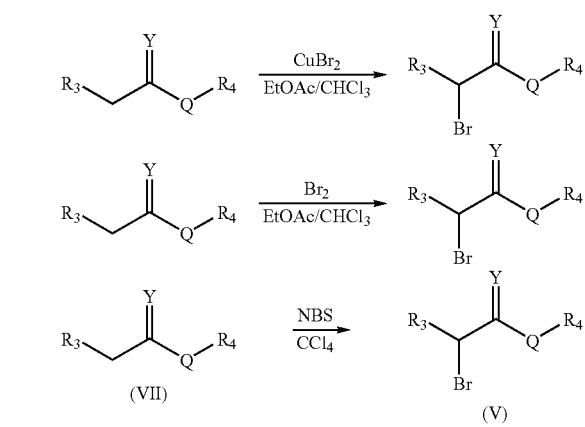

A compound of the formula (VII) is brominated at □-position with cupric bromide, bromide or NBS, to form the compound of the formula (Va). Compounds of the formula (Va) can be purified by high vacuum distillation or chromatography, wherein the silica gel used can be conventional silica gel for chromatography with a particle size of from 10 to 40 µm, and the eluent can be formulated from one or several solvents, and preferably is one of mixed solvents formulated from ethyl acetate and cyclohexane in different proportions. The compounds of the formula (Va) must be purified, to remove the small amount of α-position dibrominated product contained therein.

Optionally, the compound of the formula (I), where $R_4$ is not H, can be further hydrolyzed to form a compound of formula (Ia):

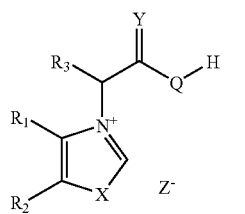

(Ia)

wherein, $R_1$, $R_2$, $R_3$, X, Y, Q, and Z are as defined above, and when Q is O, the compound of the formula (Ia) can undergo dehydration-condensation reaction with a linear or branched $C_1$-$C_8$ alkanol, a linear or branched $C_2$-$C_8$ alkenyl alcohol, a $C_3$-$C_8$ cycloalkyl alcohol, or an aromatic alcohol to form an ester.

When $R_3$ is not hydrogen, the compounds of the general formula (I) can be stereoisomers. The stereoisomers, to which the present invention may relate, can be obtained as a single optical isomer through asymmetric synthesis. However, resolution of a racemate is the main means to obtain an optically pure compound. There are mainly four methods for resolution: crystallization method, chromatographic method, kinetic method and enzymatic method. For the resolution of a racemate of the compound of the present invention, crystallization method which is of practical value is preferred: adding a chiral acid (resolution agent) to a solution of a racemate in water, in an organic solvent, or in a mixed solvent of water and an organic solvent to form diastereoisomers, and crystallizing one of the diastereoisomers first by making use of the differences in solubility of the diastereoisomers. Preferred chiral acids include tartaric acid, amygdalic acid, camphor-sulfonic acid and so on. The chromatographic method utilizes mainly various HPLC chiral columns to carry out separation, thereby giving optically pure compounds.

In a further aspect, the present invention relates to a pharmaceutical composition, comprising at least one compound of the general formula (I) or a pharmaceutically acceptable salt thereof or a hydrate thereof, and a pharmaceutically acceptable carrier or excipient. Said pharmaceutical composition can be prepared in a variety of forms depending on the administration route. The compounds according to the present invention can also be prepared as a variety of pharmaceutically acceptable salts.

The pharmaceutical composition of the present invention comprises an effective amount of a compound of the formula (I) of the present invention or a pharmaceutically acceptable salt thereof or a hydrate thereof, and one or more suitable pharmaceutically acceptable carriers or excipients. Said pharmaceutically acceptable carriers or excipients include, but are not limited to, ion exchangers, alumina, aluminum stearate, lecithin, serum proteins such as human serum albumin, buffers such as phosphate, glycerin, sorbic acid, potassium sorbate, mixtures of saturated vegetable fatty acids partially esterified with glycerin, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulosic materials, polyethylene glycol, sodium carboxymethylcellulose, polyacrylate, beeswax, and lanolin.

In a further aspect, the present invention relates to use of at least one compound of the formula (I) or a pharmaceutically acceptable salt thereof or a hydrate thereof in the preparation of medicaments for the prevention and/or treatment of various diseases resulted from glycosylation of protein.

The present invention further relates to a method of prevention and/or treatment of various diseases resulted from glycosylation of protein, comprising administering a prevention and/or treatment effective amount of at least one compound of the formula (I) or a pharmaceutically acceptable salt thereof or a hydrate thereof to a subject in need of said prevention and/or treatment.

The compounds of the present invention are a class of highly effective breaking agent for cross-linked proteins. The compounds of the present invention have better ability of breaking glycosylated proteins than that of ALT-711, thus can be used in, but not limited to, (i) increasing skin elasticity or reducing skin wrinkles, (ii) treating diabetes, (iii) treating or relieving adverse sequelae of diabetes, (iv) treating or relieving kidney damage, (v) treating or relieving damage to blood vasculature, (vi) treating or relieving hypertension, (vii) treating or relieving retinopathy, (viii) treating or relieving damage to lens proteins, (ix) treating or relieving cataract, (x) treating or relieving peripheral neuropathy, and (xi) treating or relieving osteoarthritis.

The glycosylated proteins, on which the compounds described in the present invention act, are not limited to human proteins, but also include plant proteins of crops or organ proteins of animals, thus the compounds or compositions described in the present invention can be used in fresh-keeping application.

The compounds of the present invention can be further used for the inhibition or reversal of tooth staining resulted from non-enzymatic glycosylation reaction in oral cavity. The manner using the compounds of the present invention can be altered according to the intended use.

The non-enzymatic reaction which occurs in the oral cavity can result in tooth staining. Presently used anti-plaque agents can accelerate this glycosylation reaction and further the staining of the teeth. Recently, a class of cationic bactericides with anti-plaque properties have been used in conventional oral cleaning. These cationic bactericides include alexidine, cetyl pyridinium chloride, and so on. These agents can accelerate a key step in the glycosylation reaction, i.e. Maillard reaction, to thereby accelerate tooth staining (Nordbo, J. Dent. Res., 58:1429 (1979)). Moreover, it is reported that it is observed in vitro that chlorhexidine and benzalkonium chloride can catalyze glycosylation reaction (browning reaction). Chlorhexidine added to mixtures containing a sugar and an amino acid accelerates color formation, attributed to the Maillard reaction.

Due to the above reasons, the compounds of the present invention and pharmaceutical compositions comprising the same can be used in oral cavity. Particularly suitable formulations are oral rinses and toothpastes incorporating the agents.

As for the above mentioned use of the compounds of the present invention, non-toxic and pharmaceutically acceptable carriers in appropriate forms can be used to formulate such oral rinses and toothpastes.

The pharmaceutical compositions comprising the compounds of the present invention can be administered in any of the following manners: oral administration, spraying-inhaling, rectal administration, nasal drug delivery, buccal administration, topical administration, parenteral administrations such as subcutaneous, intravenous, intramuscular, intraperitoneal, intrathecal, intraventricular, intrasternal and intracranial injection or infusion, or explantation reservoir administration, wherein oral administration, intraperitoneal or intravenous administrations are preferred.

For oral administration, the compounds of the present invention can be formed into dosage forms suitable for oral administration, including but not limited to tablets, capsules, solutions in water or suspensions in water. The carriers useful in the tablet formulations generally include lactose and corn starch, and lubricants such as magnesium stearate can also be used. Diluents useful in the capsule formulations generally include lactose and dry corn starch. Aqueous suspension formulations are generally formed by mixing active components with proper emulsifiers and suspension agents. When needed, sweeteners, flavoring agents or colorants can be added to said oral formulations.

For topical administration, especially for the treatment of suffering surfaces or organs where external applied medicaments can easily reach, such as eye, skin or lower intestine, the compounds of the present invention can be formed into various formulations suitable for topical administration depending on the suffering surfaces or organs. Detailed explanation is as follows:

When topically administered to the eye, the compounds of the present invention can be formulated into the form of micronization suspensions or solutions, wherein the carrier used is an isotonic sterile saline of a certain pH, with/without a preservative such as benzyl alkanol chloride. When administered to the eye, the compounds can also be formulated into ointment such as vaseline ointment.

When topically administered to the skin, the compounds of the present invention can be formulated into suitable forms such as ointment, lotion, or cream, wherein active components are suspended or dissolved in one or more carriers. The carriers used in the ointment formulations include, but are not limited to, mineral oil, liquid petrolatum, petrolatum album, propylene glycol, polyethylene oxide, polypropylene oxide, emulsifying wax, and water. The carriers used in the lotion or cream formulations include, but are not limited to, mineral oil, sorbitan monostearate, Tween 60, cetyl ester wax, oleyl aromatic alcohol, 2-octyl dodecanol, benzyl alcohol, and water.

The compounds of the present invention can also be administered in the form of sterile injectable preparations, including sterile injectable water or oil suspension, and sterile injectable solution. The carriers and solvents that can be used include water, Ringer's solution and isotonic sodium chloride solution. Sterile non-volatile oils such as monoglycerides or diglycerides can also be used as solvents or suspension media.

Additionally, it should be pointed out that the dosage and administration method of the compounds of the present invention are dependent on many factors, including age, body weight, gender, physical health state, nutritional status of the subject, the activity of the compounds to be used, the period of time of application, metabolic rate, severity of the disease, and the subjective judgment of the doctor. The preferred dosage is in a range of from 0.01 to 100 mg/kg body weight/day, and the most preferred dosage is in a range of from 20 to 30 mg/kg body weight/day.

EXAMPLES

The following examples are given to further illustrate the invention and by no means intended to limit the scope thereof.

Melting points of the compounds were measured by SRY-1 model melting point instrument, and the temperature was not corrected. $^1$H-NMR spectra were measured by Bruker ARX400 or US Varian Unity Inova 600 model NMR spectrometer, and FAB mass spectra were measured by Zabspect high resolution mass spectrometer.

General Procedure: general procedure for the reaction between thiazole parent nuclei and α-bromo-esters

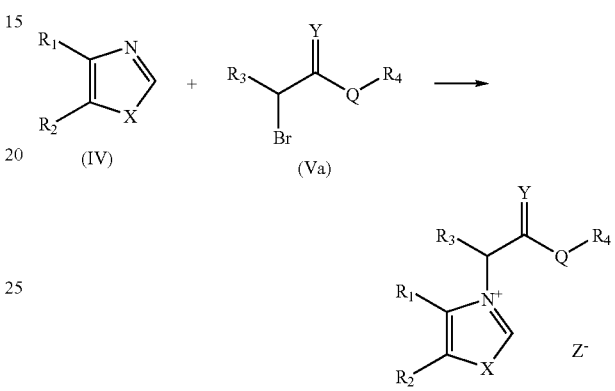

The reaction between a thiazole parent nucleus and an α-bromo-ester compound according to the above reaction route was conducted in the presence of a solvent, such as ethanol, acetonitrile or butanone, or in the absence of a solvent when one of the above two raw materials is a liquid, at a temperature of 80° C. to 100° C. under nitrogen atmosphere for 5 to 96 hours.

The reaction products were purified by using still standing crystallization and then recrystallization or by using silica gel column chromatography. The silica gel used was conventional silica gel for chromatography with a particle size of from 10 to 40 μm, and the eluent was formulated from one or several solvents, and exemplified by mixed solvents formulated from dichloromethane and methanol in different proportions. After purification, target compounds were obtained.

Example 1

3-benzyloxycarbonylmethyl-4,5-dimethyl-thiazole-3-bromide

According to the above general procedure, the title compound (0.4 g, yield 26%, oily substance) was prepared from benzyl bromoacetate and 4,5-dimethyl-thiazole.

MS[M$^+$]=262.1 m/e; $^1$H-NMR (400 MHz, DMSO) δ 2.349 (s 3H); 2.510 (s 3H); 5.273 (s 2H); 5.728 (s 2H); 7.416-7.427 (m 5H); 10.104 (s 1H).

Example 2

3-benzyloxycarbonylmethyl-5-(2-hydroxyethyl)-4-methyl-thiazole-3-bromide

The title compound (0.5 g, yield 28%, oily substance) was prepared according to the method of Example 1, except that benzyl bromoacetate and 5-(2-hydroxyethyl)-4-methyl-thiazole were used.

MS[M+]=292.1 m/e; $^1$H-NMR (400 MHz, DMSO) δ 2.322 (s 3H); 3.016 (t J=5.2 Hz 2H); 3.769 (t J=5.2 Hz 2H); 5.213 (s 2H); 5.730 (s 2H); 7.337-7.356 (m 5H); 10.521 (d J=5.5 Hz 1H).

Example 3

3-benzyloxycarbonylmethyl-4-methyl-thiazole-3-bromide

According to the general procedure, the title compound (1.2 g, yield 30%, oily substance) was prepared from benzyl bromoacetate and 4-methyl-thiazole.

MS[M+]=313.9 m/e; $^1$H-NMR (400 MHz, $CD_3OD$) δ 2.512 (s 3H); 5.293 (s 2H); 5.600 (s 2H); 7.356-7.399 (m 5H); 7.991 (s 1H).

Example 4

3-benzyloxycarbonylmethyl-4,5,6,7-tetrahydro-benzothiazole-3-bromide

According to the general procedure, the title compound (1.3 g, yield 31%, light yellow solid, m. p. 160-166° C.) was prepared from benzyl bromoacetate and 4,5,6,7-tetrahydro-benzothiazole.

MS[M+]=288.0 m/e; $^1$H-NMR (400 MHz, DMSO) δ 1.798 (m 4H); 2.681 (m 2H); 2.903 (t J=4.3 Hz 2H); 5.269 (s 2H); 5.702 (s 2H); 7.312-7.423 (m 5H); 10.172 (s 1H).

Example 5

3-carboxymethyl-4-methyl-thiazole-3-bromide 1 g of 3-benzyloxycarbonylmethyl-4-methyl-thiazole-3-bromide as obtained in Example 3 was dissolved in 1N aqueous solution of $KCO_3$ and stirred at room temperature for 3 hours, during which TLC was used to monitor the reaction. At the end of the reaction, the reaction mixture was extracted with 10 ml×3 of chloroform, and aqueous layer was separated. With ice-bath cooling, to the water layer was added dropwise 1N HBr aqueous solution till the solution had a pH value of 2. Then the aqueous solution was evaporated to dryness. 20 of anhydrous ethanol was added to wash the residues, then insoluble substances were removed by filtration. The obtained ethanol solution was evaporated to dryness, to thereby obtain the title compound as tan solids (700 mg, yield 50%, m. p. 223-230° C.).

MS[M+]=158.2 m/e; $^1$H-NMR (400 MHz, DMSO) 2.3606 (d J=0.8 Hz 3H); 5.0936 (s 2H); 7.7131 (d J=1.7 Hz 1H); 9.7258 (d J=2.8 Hz 1H).

Example 6

Elisa Screening Experiment on the Breaking of AGE-BSA Collagen Cross-Links

AGE cross-links were prepared in vitro by cross-linking AGE-BSA to rat tail tendon collagen-coated 96 well microtiter plates. ELISA method was used to evaluate the breaking effect of the compounds on AGE cross-links.

Preparation of the Tail Collagen-Coated 96 Well Microtiter Plates:

Normal Wister rats (body weight 200±20 g) were sacrificed acutely, then the tails were excised, and tail collagen was prepared at a temperature of 4° C. as follows: tail tendon collagen fibrils were taken out, washed with physiological saline, peeled off non-collagen fibril tissue, rinsed with distilled deionized water 3 times, cut into pieces, and immersed in 0.1% acetic acid at 4° C. for one week during which the immersion liquid was shaken frequently. Finally, the immersion liquid was subjected to a centrifuge treatment at 8000 G for 30 minutes, and supernatant collagen solution was collected. After dilution, protein content was measured. 96 well microtiter plates (Costar) were full-well coated with the collagen solution in an amount of 70 μg/well at 4° C. for 24 hours, then the coating solution was discarded. The plates were dried in air under sterile condition, coated with a fresh-keeping film, and finally stored at 4° C. for use.

AGE-BSA Preparation:

A solution containing 50 mg/ml of bovine serum albumin BAS (V) (Roch) and 0.5M of glucose in 0.2M PBS (pH 7.4) was incubated at 37° C. under sterile condition for 3-4 months, to thereby form glycosylated BSA, i.e. BSA-AGE. At the same time, non-glycosylated BSA was prepared with glucose-free BSA. Then the BSA-AGE solution was dialyzed against 0.01M PBS (pH 7.4) to be removed of unreacted glucose. Fluorescence scanning (Exi/Em (395/460 nm)) and SDS-PAGE were used to check the formation of BSA-AGE, and protein concentration was determined by the Lowery method.

Assay Protocol:

The tail collagen-coated 96 well microtiter plates were full-well treated with PBS (pH 7.4) for 1 hour to neutralize the acidic collagen. Then the plates were blocked with Superblock (PIERCE) at 37° C. for 1 hour, and washed with PBST (PBS-Tween) three times while shaking for 1 minute for each time of washing. AGE-BSA was diluted in PBS to a concentration required to obtain maximum cross-linking. 100 μl of the AGE-BSA solution was added to wells in the rows labeled as A, B, C, and D of the 96 well plates, and BSA solution of the same concentration was added to wells in the rows labeled as E, F, G, and H. The first three wells in each row were filled with PBS for the reagent blank. The plates were incubated at 37° C. for 4 hours to allow the collagen crosslink, and washed with PBST four times while shaking for 1 minute for each time of washing. Test compounds were diluted in PBS of pH 7.4. A test compound was added to quadruplicate AGE-BSA cross-links wells and quadruplicate BSA wells in an amount of 100 μl/well. PBS was added in an amount of 100 μl/well in the same way as non-breaking contrast. The plates were incubated at 37° C. for 16 hours and washed four times with PBST while shaking for 1 minute for each time of washing. 80 μl/well of Rabbit-anti-BSA antibody (1:500) was added to the wells and the plates were incubated at 37° C. for 50 minutes. After the plates were washed with PBST four times while shaking for 1 minute for each time of washing, 80 μl/well of horseradish peroxidase-labelled-goat-anti-rabbit IgG (1:1000) was added to the wells. The plates were incubated at 37° C. for 50 minutes, and then washed with PBST three times while shaking for 1 minute for each time of washing. 100 μl/well of TMB substrate (3,3',5,5'-tetramethylbenzidine) was added to the wells. The plates were incubated at room temperature at dark place for 20 minutes. 2M $H_2SO_4$ was used to terminate the reaction. Within 10 minutes after the reaction, optical density was read at 450 nm on the BOBRAD Model 550 plate reader with the blank wells of the plates was set to 0.

Data Analysis:

The average optical density (OD) was calculated for each quadruplicate determination.

Corrected OD=Average of OD AGE-BSA wells−Average of OD BSA wells

Percent breaking was expressed as the percent decrease in OD:

[(Average of OD PBS wells−Average of OD test compound wells)/Average of OD PBS wells]×100%

The breaking rates of the test compounds at concentrations of 0.1 and 1 mmol/L as determined according to the above protocol are shown in Table 1 (the results are averages of more than three screening results).

TABLE 1

Breaking rates of compounds on AGE-BSA-collagen cross-links determined through ELISA

| Compound | Breaking rate (decrease % in OD) | |
| --- | --- | --- |
|  | 1 (mmol/L) | 0.1 (mmol/L) |
| ALT-711 | 15.2 ± 8.43 | 13.4 ± 6.41 |
| 1 | 10.81 ± 3.86 | 9.65 ± 3.55 |
| 2 | 13.25 ± 10.29 | 13.5 ± 9.53 |
| 3 | 26.46 ± 18.2 | 16.16 ± 7.07 |
| 4 | 7.17 ± 2.40 | 8.45 ± 5.35 |
| 5 | — | — |

The invention claimed is:

1. A compound of general formula (I),

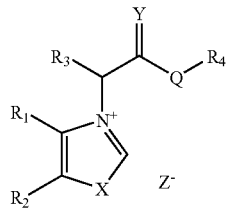

wherein:
X is S,
Y is O,
Q is O,
$R_1$ is methyl, or is bonded with $R_2$ to form a 6-membered aliphatic ring,
$R_2$ is methyl, or is bonded with $R_1$ to form a 6-membered aliphatic ring,
$R_3$ is hydrogen,
$R_4$ is benzyl,
and $Z^-$ is a pharmaceutically acceptable acid radical,
or a pharmaceutically acceptable salt thereof.

2. The compound according to claim 1, wherein:
$Z^-$ is $F^-$, $Cl^-$, $Br^-$, methanesulfonate, or p-methylbenzenesulfonate,
or pharmaceutically acceptable salt thereof.

3. A compound selected from the group consisting of:
3-benzyloxycarbonylmethyl-4,5-dimethyl-thiazole-3-bromide,
3-benzyloxycarbonylmethyl-4-methyl-thiazole-3-bromide, and
3-benzyloxycarbonylmethyl-4,5,6,7-tetrahydro-benzothiazole-3-bromide,
or a pharmaceutically acceptable salt thereof.

4. A pharmaceutical composition comprising a compound according to claim 1 or a pharmaceutically acceptable salt thereof, and at least one pharmaceutically acceptable carrier or excipient.

5. A method for preparing the compound according to claim 1, or a compound of formula (Ia) or an ester of the compound of formula (Ia), comprising:
reacting a compound of formula (IV):

with a compound of formula (V)

wherein L is a leaving group, such as F, Cl, Br, I, methanesulfonato, or p-methylbenzenesulfonato, to obtain the compound of the general formula (I)

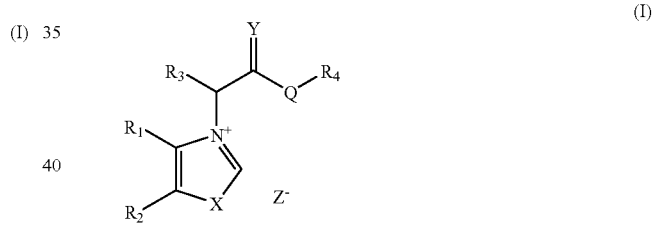

optionally, further hydrolyzing the compound of the general formula (I), to obtain a compound of formula (Ia):

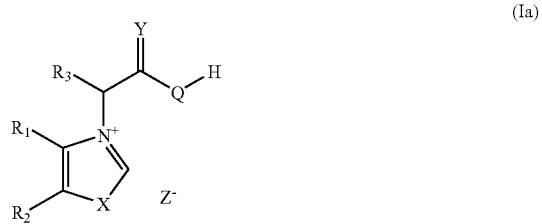

and optionally, reacting the compound of the formula (Ia) with a linear or branched $C_1$-$C_8$ alkanol, a linear or branched $C_2$-$C_8$ alkenyl alcohol, a $C_3$-$C_8$ cycloalkyl alcohol, or an aromatic alcohol, to obtain an ester of the compound of formula (Ia),
wherein $R_1$, $R_2$, X, $R_3$, Y, Q, $R_4$ and $Z^-$ are as defined in claim 1.

* * * * *